United States Patent [19]

Moeller et al.

[11] Patent Number: 4,683,244
[45] Date of Patent: Jul. 28, 1987

[54] SEBOSUPPRESSIVE COSMETIC PREPARATIONS CONTAINING ALKOXY OR ALKYLBENZYLOXY BENZOIC ACIDS OR THEIR SALTS

[75] Inventors: Hinrich Moeller; Siegfried Wallat, both of Monheim, Fed. Rep. of Germany

[73] Assignee: Henkel Kommanditgesellschaft auf Aktien, Duesseldorf, Fed. Rep. of Germany

[21] Appl. No.: 818,502

[22] Filed: Jan. 10, 1986

[30] Foreign Application Priority Data

Jan. 14, 1985 [DE] Fed. Rep. of Germany ....... 3500972

[51] Int. Cl.$^4$ ............................................... C07C 65/00
[52] U.S. Cl. ..................................... 514/568; 562/473
[58] Field of Search ......................... 562/473; 514/568

[56] References Cited

U.S. PATENT DOCUMENTS 4,503,244 3/1985 Moeller et al. ..................... 514/544
4,545,984 10/1985 Moeller et al. ..................... 424/70

FOREIGN PATENT DOCUMENTS 2021227 11/1970 Fed. Rep. of Germany .
2439458 2/1975 Fed. Rep. of Germany .

OTHER PUBLICATIONS

Baggaley K. et al., J. Med. Chem., 20(11), 1388-93, 1977.

*Primary Examiner*—Paul J. Killos
*Attorney, Agent, or Firm*—Ernest G. Szoke; Henry E. Millson, Jr.; Mark A. Greenfield

[57] ABSTRACT

A cosmetic preparation for the treatment of seborrhea containing an antiseborrheically effective amount of a p-alkoxy or p-alkybenzyloxy benzoic acid or salt thereof having the formula

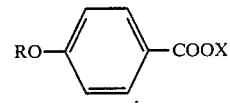

wherein R is either an alkyl group having from 6 to 18 carbon atoms, or an alkybenzyl group wherein the alkyl moiety has from 3 to 9 carbon atoms, and X is a member selected from the group consisting of hydrogen, an alkali metal, an alkaline earth metal and ammonium, and further containing conventional vehicles and additives; the process for reducing mammalian sebum production by using the above cosmetic preparation; and certain p-alkoxy and p-alkylbenzyloxy benzoic acids or salts thereof of the above formula.

20 Claims, No Drawings

SEBOSUPPRESSIVE COSMETIC PREPARATIONS CONTAINING ALKOXY OR ALKYLBENZYLOXY BENZOIC ACIDS OR THEIR SALTS

BACKGROUND OF THE INVENTION

1. Field of the Invention

This invention relates to topical cosmetic preparations for improving the oily and unaesthetic appearance of hair and skin. This invention particularly relates to cosmetic preparations containing certain alkoxy or alkylbenzyloxy benzoic acids or their salts.

2. Description of Related Art

In modern cosmetology, researchers continue to look for cosmetic preparations which will reduce the oily and unaesthetic appearance of the hair and scalp caused by excessive secretion of the sebaceous glands. By treating hair and scalp with suitable cosmetic preparations, secretion of the sebaceous glands may be reduced to their normal level and oily hair may be restored to a healthy appearance.

In the past, cosmetic preparations such as shampoos containing sulfur, mercury or tar additives have been used to control seborrhea of the scalp. Unfortunately, prolonged use of these known antiseborrheic additives frequently caused unwanted side effects, without giving really satisfactory results with regard to efficacy and performance properties. Derivatives of benzoic acid esters also have been described as antiseborrheic additives for cosmetic preparations (see U.S. Pat. Nos. 4,503,244 and 4,545,984). Nonetheless, a need still exists for topical cosmetic preparations showing enhanced sebosuppressive activity.

An object of the present invention is to provide a cosmetic preparation which exhibits an improved antiseborrheic activity as compared with known preparations but does not contribute to any adverse consequences on the human body.

DESCRIPTION OF THE INVENTION

It has now been found, quite unexpectedly, that certain alkoxy or alkylbenzyloxy benzoic acids and their salts possess outstanding antiseborrheic activity, even in very small doses. Surprisingly, the antiseborrheic effect obtained using these materials is considerably better than that obtained using known benzoic acid esters. Consequently, these alkoxy or alkylbenzyloxy benzoic acids and salts can be used in smaller quantities in sebosuppressive cosmetic preparations.

Accordingly, the present invention relates to a sebosuppressive cosmetic preparation containing an antiseborrheically effective amount of a p-alkoxy or p-alkylbenzyloxy benzoic acid, or a salt thereof, corresponding to the following formula

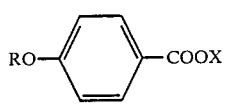

(I)

wherein R is either an alkyl group having from 6 to 18 carbon atoms, or an alkylbenzyl group wherein the alkyl moiety has from 3 to 9 carbon atoms, and X is a member selected from the group consisting of hydrogen, an alkali metal, an alkaline earth metal and ammonium. Generally, the sebosuppressive cosmetic preparation further includes conventional vehicles and additives for facilitating topical application.

The present invention also relates to a process for reducing the production of sebum by the sebaceous cell in mammals which comprises contacting said sebaceous cell with an antiseborrheically effective amount of the compound of formula I, as defined above.

While some of the compounds used in accordance with the present invention are known from the literature, others are new. Thus, the present invention further relates to a p-alkoxy or p-alkylbenzyloxy benzoic acid or salt thereof having the formula

(II)

in which R is a member selected from the group consisting of isononyl, isotridecyl and 4-tert-butylbenzyl, and X is selected from the group consisting of hydrogen, an alkali metal, an alkaline earth metal and ammonium, which are believed to be novel compounds.

Compounds useful in practicing the present invention may be produced by generally known methods of organic chemistry. For example a p-hydroxybenzoic acid ester can be alkylated with an alkyl halide, an alkyl sulfate or an alkyl sulfonate containing a linear or branched alkyl or alkylbenzyl group (preferably a p-alkylbenzyl group) corresponding to the desired R substituent to produce a p-alkoxy or p-alkylbenzyloxy benzoic acid ester. Preferably, the methyl or ethyl esters of p-hydroxybenzoic acid are used as the starting material. Alkaline hydrolysis of the p-alkoxy or p-alkylbenzyloxy benzoic acid ester produces the desired p-alkoxy or p-alkylbenzyloxy benzoic acid or salt thereof. As will be recognized by those skilled in this art, any of a wide variety of alkaline materials can be used. Preferably a water soluble material such as an alkali metal or alkaline earth metal hydroxide or ammonium hydroxide is used. Particularly preferred are sodium, potassium, lithium, calcium or ammonium bases. Conventional purification techniques can be employed to recover the p-alkoxy or p-alkylbenzyloxy benzoic acid in either its free acid form or its salt form, e.g., treatment of the hydrolysis product with a strong acid such as HCl.

Examples of antiseborrheic compounds useful for preparing a sebosuppressive cosmetic preparation according to the present invention are 4-hexyloxy, 4-heptyloxy, 4-octyloxy, 4-(2,4,4-trimethylpentyloxy), 4-(2-ethylhexyloxy), 4-nonyloxy, 4-decyloxy, 4-undecyloxy, 4-dodecyloxy, 4-isotridecyloxy, 4-tetradecyloxy, 4-hexadecyloxy, 4-octadecyloxy, 4-isononyloxy, 4-(4-tert-butylbenzyloxy) benzoic acids and the Na, K, Li, NH4 and Ca salts thereof.

Particularly preferred sebosuppressive cosmetic preparations are those containing p-alkoxy or p-alkylbenzyloxy benzoic acids or salts thereof of formula I in which the R radical is an alkyl group having from 9 to 14 carbon atoms or is p-tert-butylbenzyl.

The compounds of the present invention show pronounced sebosuppressive activity combined with excellent compatibility with the skin and mucous membrane. They may be incorporated without difficultly in various cosmetic preparations, such as aqueous or alcoholic solutions, oils, suspensions, gels, emulsions, salves or aerosols. The greater solubility in water and resistance to hydrolysis of these p-alkoxy and p-alkylbenzyloxy benzoic acids and salts as compared with the corresponding esters are particularly advantageous for the preparation of such products. For treating seborrheic skin and oily hair, these preparations may be applied in any of the usual forms, such as hair lotions, shampoos, hair treatments, hair rinses, skin lotions or shaking mixtures containing any of the conventional vehicles and additives for facilitating topical application. A shampoo is a particularly effective form for treating very oily hair.

The cosmetic preparations according to the invention represent solutions and dispersions of an effective amount of the compounds of formula I in water, in alcohol—especially ethanol, in aqueous-alcoholic mixtures, in oil, as well as in suspensions, gels, emulsions, salves, pastes, or aerosols. Preferably these p-alkoxy and p-alkylbenzyloxy benzoic acid and salts are used as an ingredient in known hair care preparations. In addition to including an active substance according to the invention, these cosmetic preparations may contain standard auxiliaries and vehicles, such as water, organic solvents, surfactants, oils, fats, waxes, fragrances, dyes, preservatives and the like.

Preferably, the sebosuppressive preparation contains from about 0.005 to 5% by weight and more preferably from about 0.01 to 2% by weight of the p-alkoxy or alkylbenzyloxy benzoic acid or salt thereof. As will be demonstrated in the Examples which follow, due to the improved antiseborrheic activity of the p-alkoxy and p-alkylbenzyloxy benzoic acids of this invention, sebosuppressive cosmetic preparations can be formulated having a much lower amount of the active substance than was possible using prior art materials.

While preparations according to the invention can be used daily, satisfactory results also can be obtained using a single weekly application. By employing the cosmetic preparations of this invention, the oily appearance of hair is reduced, and fat production delayed, so that normal hair care is possible. The individual dose to be used in each treatment is not critical and harmful side effects have not been observed.

The following examples are presented to illustrate further the present invention and are not intended to limit its scope which is defined by the appended claims.

PRODUCTION EXAMPLES (A) Preparation of 4-tetradecyloxy benzoic acid

Twenty grams of tetradecyloxy benzoic acid methyl ester and 2.75 g of sodium hydroxide were dissolved in 80 ml of ethanol. After the addition of 50 ml of water was heated for 2.5 hours to boiling temperature. The resulting suspension was concentrated by evaporation and the evaporation residue was dissolved in hot water. The solution then was acidified with dilute hydrochloric acid, filtered, washed with water and dried. 4-tetradecyloxybenzoic acid melting at 95° to 99° C. (clear at 135° C. was obtained in a yield of 18.2 g, corresponding to 95% of the theoretical.

The following acids were obtained by an analogous procedure to that used in Preparation procedure (A) using the appropriate alkoxy or alkylbenzyloxy benzoic acid methyl ester as the starting material:

(B) Preparation of 4-dodecyloxy benzoic acid

The acid product recovered exhibited a melting point of 94°–95° C. (clear at 135° C.).

(C) Preparation of 4-decyloxy benzoic acid

The acid product recovered exhibited a melting point of 97°–98° C. (clear at 120° C.).

(D) Preparation of 4-isononyloxy benzoic acid

The acid product recovered exhibited a melting point of 118°–119° C.

(E) Preparation of 4-(4-tert-butylbenzyloxy)-benzoic acid

The acid product recovered exhibited a melting point of 236°–239° C.

(F) Preparation of 4-isotridecyloxy benzoic acid

The acid product recovered exhibited a melting point of 56° C. (beyond 36° C. sintering).

TESTING FOR ANTI-SEBORRHEIC ACTIVITY

The anti-seborrheic effect obtained with compounds (B)-(F) prepared above was closely examined using the following animal tests.

Male Wistar rats having a body weight ranging from 220 to 230 g at the beginning of the tests were used as the test animals. The accumulation of sebum in the test animals was examined by visually observing the degree of browning on the shaved back of the rats. Browning is caused by the accumulation of the brown skin surface lipid secreted by the rats. This test is based on the observation that young female rats, as well as male rats washed with a surfactant solution or with a lipid solvent or male rats systematically treated with estrogens show only a normal light, pink-colored skin after shaving, while at the same time, only comparatively very small quantities of lipids can be extracted from the shaved hairs.

In order to assess the anti-seborrheic effectiveness of the p-alkoxy and p-alkylbenzyloxy benzoic acids, alcoholic solutions of test substances (B) through (F) were each brushed onto one side of the back of 6 rats. The p-alkoxy or P-alkylbenzyloxy benzoic acids tested were applied in concentrations ranging from 0.01 to 0.5 wt. % in the alcohol. The other side of the back of each rat was treated only with solvent without an active substance (control side).

The test period consisted of 14 days. The test substances were applied, once daily on 9 of the 14 days. A second group of 6 rats which were not treated was used as an additional control. At the end of the test period, the backs and sides of the animals were shaved and visually inspected. The examination was done independently by an evaluation panel composed of 6 people using double blind techniques.

EVALUATION METHODS

The rats can be rated on the basis of two criteria. A first criterion is the difference in coloration between the righthand side and the lefthand side of the treated rats. Each examiner awards 1 point per animal on the following basis:

| | |
|---|---|
| darker side | 1 point |
| lighter side | 0 point and |
| both sides the same | 0.5 point |

A significant difference between an untreated and treated side in this method of evaluation indicates the local effectiveness of a substance.

A second criterion of evaluation is the intensity of the brown coloration in the shaved area. The following scale is used for this analysis:

3 points dark brown
2 points medium brown
1 point light brown
0 points no browning According to this second method of evaluation, differences in the total points between the untreated control animals and the treated and untreated sides (ΔP) of the test animals respectively are calculated. Significant differences between the total point values assigned to the control animals and the values assigned to the treated side of the test animals again indicate the antiseborrheic effectiveness of a substance.

At the same time, there also generally is a distinct difference between the values assigned to the untreated and treated sides of the test animals. However, due to various reasons, including for example mechanical transfer of substance from one side of the animal to the other or solvent influence, this difference is not always as distinct as that observed between the control animals and the treated side of the test animals.

The following analysis scheme can be used to differentiate and quantify the effects observed according to evaluation methods 1 and 2:

| Symbol | Point difference |
|---|---|
| ++ | very large (≧99.9% probability) |
| + | significant (≧95% probability) |
| − | (<95% probability) |

PERCENT SEBUM REDUCTION

Results obtained with the animals tested as outlined above using the second evaluation method are set forth in the following Table. The results are presented in terms of sebum reduction percentage. The sebum reduction percentage is calculated from the point differences by determining the quotient of the difference in total points between the control group and the treated side of the test animals (ΔP) and the total number of points for the control group ($P_k$) and then expressing the value obtained in percent.

$$\text{Percent Sebum reduction} = \frac{\Delta P}{P_k} \cdot 100[\%]$$

TABLE

| | Evaluation of the sebosuppressive effects | | | |
|---|---|---|---|---|
| Compound Tested | % Sebum reduction at the indicated concentration of active substance | | | |
| | 0.1% | 0.05% | 0.01% | 0.001% |
| B | 92 | 76 | 35 | — |
| C | 42 | — | — | — |
| D | 90 | 68 | — | — |
| E | 95 | — | — | — |
| F | — | 83 | 70 | 21 |
| 4-dodecyloxy benzoic acid methyl ester (U.S. Pat. No. 4,545,984) | 18 | 0 | — | — |
| 4-dodecyloxy benzoic acid-2-methoxyethyl ester (U.S. Pat. No. 4,503,244) | 22 | — | — | — |

TABLE-continued

| | Evaluation of the sebosuppressive effects | | | |
|---|---|---|---|---|
| Compound Tested | % Sebum reduction at the indicated concentration of active substance | | | |
| | 0.1% | 0.05% | 0.01% | 0.001% |

The superior effect of the compounds used in the present invention relative to the benzoic acid esters of the prior art is clear from the values shown in the Table.

EXAMPLES OF FORMULATIONS

Specific formulations for topical cosmetic preparations of the present invention useful for the treatment of very oily hair and seborrheic skin are presented below:

| | Percent by weight |
|---|---|
| 1. Shampoo for oily hair | |
| Ammonium lauryl sulfate containing 33 to 35% of washing-active substance | 40.0 |
| Coconut oil fatty acid diethanolamide | 3.0 |
| Sodium chloride | 2.0 |
| Sodium sulfate | 2.0 |
| 4-dodecyloxy benzoic acid (compound B) | 1.0 |
| Preservative | 0.1 |
| Perfume oil | 0.1 |
| Water | 51.8 |
| pH adjustd to 7.2 (with sodium hydroxide) | |
| 2. Hair treatment | |
| Glycerol mono-distearate | 0.7 |
| Cationic surfactant (for example lauryl trimethylammonium chloride) | 2.0 |
| Cholesterol | 0.2 |
| Soya lecithin | 0.3 |
| A mixture of cetylstearyl alcohol with nonionic emulsifiers ("Emulgade"A - *) | 7.0 |
| Perfume oil | 0.3 |
| 4-isononyloxy benzoic acid (compound D) | 2.0 |
| Water, fully deionized | 87.5 |
| pH adjusted to 6.5 (sodium hydroxide) | |
| 3. Skin cream | |
| Self-emulsifying mixture of mono/diglycerides of higher saturated fatty acids with potassium stearate "Cutina" KD 16 (*) | 16.0 |
| Cetylstearyl alcohol containing approx. 12 moles of ethylene oxide "Eumulgin" B1 (*) | 1.0 |
| 2-octyldodecanol | 6.0 |
| Isopropylmyristate | 4.0 |
| Glycerol | 6.0 |
| 4-(4-tert-butylbenzyloxy)benzoic acid (compound E) | 0.4 |
| Preservative (for example 4-hydroxybenzoic acid methylester) | 0.1 |
| Water | 66.5 |

(* - a trademark of Henkel KGaA, Federal Republic of Germany)

Although certain embodiments of the invention have been described in detail, it will be appreciated that other embodiments are contemplated along with modification of the disclosed features, as being within the scope of the invention, which is defined in the appended claims.

We claim:

1. A sebosuppressive cosmetic composition containing a solution, mixture, or dispersion, in a base comprising at least one of water, alcohol, or oil, of an antiseborrheically effective amount of a p-alkoxy or p-alkylbenzyloxy benzoic acid, or a salt thereof, corresponding to the following formula:

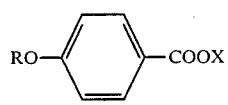

wherein R is either an alkyl group having from 6 to 18 carbon atoms, or an alkylbenzyl group wherein the alkyl moiety has from 3 to 9 carbon atoms, and X is a member selected from the group consisting of hydrogen, an alkali metal, an alkaline earth metal and ammonium.

2. The sebosuppressive cosmetic composition of claim 1 wherein R is either an alkyl group having from 9 to 14 carbon atoms or p-tert-butylbenzyl.

3. The sebosuppressive cosmetic composition of claim 1 wherein X is a member selected from the group consisting of hydrogen, lithium, sodium, potassium, calcium and ammonium.

4. The sebosuppressive cosmetic composition of claim 2 wherein X is a member selected from the group consisting of hydrogen, lithium, sodium, potassium, calcium and ammonium.

5. The sebosuppressive cosmetic composition of claim 1 wherein said antiseborrheically effective amount comprises between about 0.005 and 5.0 wt. %, of the total weight of said preparation.

6. The sebosuppressive cosmetic composition of claim 2 wherein said antiseborrheically effective amount comprises between about 0.005 and 5.0 wt. %, of the total weight of said preparation.

7. The sebosuppressive cosmetic composition of claim 5 wherein said antiseborrheically effective amount comprises between about 0.01 and 2.0 wt. %, of the total weight of said preparation.

8. The sebosuppressive cosmetic composition of claim 6 wherein said antiseborrheically effective amount comprises between about 0.01 and 2.0 wt. %, of the total weight of said preparation.

9. A method for reducing the production of sebum by the sebaceous cell in mammals which comprises topically contacting said sebaceous cell with an antiseborrheically effective amount of a p-alkoxy or a p-alkylbenzyloxy benzoic acid, or a salt thereof, corresponding to the following formula

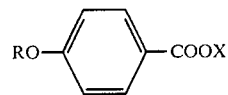

wherein R is either an alkyl group having from 6 to 18 carbon atoms, or an alkylbenzyl group wherein the alkyl moiety has from 3 to 9 carbon atoms, and X is a member selected from the group consisting of hydrogen, an alkali metal, an alkaline earth metal and ammonium.

10. The method of claim 9 wherein R is either an alkyl group having from 9 to 14 carbon atoms or p-tert-butylbenzyl.

11. The method of claim 9 wherein X is a member selected from the group consisting of hydrogen, lithium, sodium, potassium, calcium and ammonium.

12. The method of claim 10 wherein X is a member selected from the group consisting of hydrogen, lithium, sodium, potassium, calcium and ammonium.

13. The method of claim 9 wherein said antiseborrheically effective amount comprises between about 0.005 and 5.0 wt. % of the total wt.

14. The method of claim 10 wherein said antiseborrheically effective amount comprises between about 0.005 and 5.0 wt. % of the total wt.

15. The method of claim 13 wherein said antiseborrheically effective amount comprises between about 0.01 and 2.0 wt. % of the total wt.

16. The method of claim 14 wherein said antiseborrheically effective amount comprises between about 0.01 and 2.0 wt. % of the total wt.

17. The sebosuppressive cosmetic composition of claim 1 wherein said antiseborrheically effective compound is:
  4-dodecyloxy benzoic acid; 4-isononyloxy benzoic acid; or
  4-(4-tert-butylbenzyloxy) benzoic acid.

18. The sebosuppressive cosmetic composition of claim 1 consisting essentially of said antiseborrheic benzoic acid compound, at least one of water, organic solvent, surfactant, oil, fat, wax, fragrance, dye, or preservative.

19. The sebosuppressive cosmetic composition of claim 18 comprising a shampoo for oily hair further containing a surfactant.

20. The sebosuppressive cosmetic composition of claim 18 comprising a hair treatment preparation further containing an alcohol and a surfactant.

21. The sebosuppressive cosmetic composition of claim 18 comprising a skin cream further containing alcohol, glycerol, and glycerides.

* * * * *